(12) United States Patent
Morfill et al.

(10) Patent No.: US 10,300,159 B2
(45) Date of Patent: May 28, 2019

(54) METHOD FOR DEACTIVATING PREFERABLY ODOR-RELEVANT MOLECULES AND DEVICE FOR CARRYING OUT SAID METHOD

(75) Inventors: Gregor Morfill, Munich (DE); Tetsuji Shimizu, Garching (DE); Julia Zimmermann, Munich (DE); Yangfang Li, Garching (DE); Bernd Steffes, Oberammergau (DE)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 86 days.

(21) Appl. No.: 14/115,783

(22) PCT Filed: May 4, 2012

(86) PCT No.: PCT/EP2012/001923
§ 371 (c)(1),
(2), (4) Date: Jan. 24, 2014

(87) PCT Pub. No.: WO2012/150040
PCT Pub. Date: Nov. 8, 2012

(65) Prior Publication Data
US 2014/0147333 A1 May 29, 2014

(30) Foreign Application Priority Data

May 5, 2011 (DE) .......... 10 2011 100 751
Nov. 19, 2011 (DE) .......... 10 2011 118 996

(51) Int. Cl.
*A61L 2/14* (2006.01)
*B01D 53/32* (2006.01)
(Continued)

(52) U.S. Cl.
CPC .......... *A61L 2/14* (2013.01); *A61L 9/22* (2013.01); *B01D 53/32* (2013.01); *F24C 15/20* (2013.01);
(Continued)

(58) Field of Classification Search
CPC ... A61L 2/14; A61L 9/22; B01D 53/32; F24C 15/20; H05H 1/2406
(Continued)

(56) References Cited

U.S. PATENT DOCUMENTS 8,263,004 B2 * 9/2012 Nishikawa ............ A61L 2/0011
204/194
2005/0000054 A1 * 1/2005 Ninomiya ................. A47L 7/04
15/347
(Continued)

FOREIGN PATENT DOCUMENTS

DE       10254135 B3     6/2004
DE   202006009481 U1    11/2006
(Continued)

OTHER PUBLICATIONS

Muller, S. (2010)."Smell reduction and disinfection of textile materials bydielectric barrier discharges." Natural Science. 2(9): 1044-1048.*
(Continued)

*Primary Examiner* — Jill A Warden
*Assistant Examiner* — Jacqueline Brazin
(74) *Attorney, Agent, or Firm* — Caesar Rivise, PC

(57) ABSTRACT

A method for deactivating preferably odor-relevant molecules that is distinguished by the following steps is proposed: generating a plasma; deactivating preferably odor-relevant molecules by the effect of hot electrons of the plasma on the molecules to be deactivated.

9 Claims, 3 Drawing Sheets

(51) Int. Cl.
*H05H 1/24* (2006.01)
*A61L 9/22* (2006.01)
*F24C 15/20* (2006.01)
*A61N 5/06* (2006.01)

(52) U.S. Cl.
CPC ......... *H05H 1/2406* (2013.01); *A61N 5/0624* (2013.01); *B01D 2257/90* (2013.01); *B01D 2257/91* (2013.01); *B01D 2259/818* (2013.01); *H05H 2001/2418* (2013.01)

(58) Field of Classification Search
USPC .......................................................... 422/5
See application file for complete search history.

(56) References Cited

U.S. PATENT DOCUMENTS

| | | | |
|---|---|---|---|
| 2005/0171528 A1 | 8/2005 | Sartor et al. | |
| 2007/0208337 A1 | 9/2007 | Podhajsky et al. | |
| 2007/0253865 A1 | 11/2007 | Tsutsui et al. | |
| 2008/0193329 A1* | 8/2008 | Akishev ................ | H05H 1/24 422/22 |
| 2009/0069741 A1 | 3/2009 | Altshuler et al. | |
| 2011/0022043 A1* | 1/2011 | Wandke ................ | A61N 1/40 606/41 |
| 2011/0034914 A1 | 2/2011 | Auge, II et al. | |
| 2012/0111359 A1 | 5/2012 | Mueller et al. | |
| 2012/0271225 A1 | 10/2012 | Stieber et al. | |

FOREIGN PATENT DOCUMENTS

| | | |
|---|---|---|
| DE | 202009011521 U1 | 2/2011 |
| EP | 2170022 A1 | 3/2010 |
| GB | 2454461 A | 5/2009 |
| WO | 2008028564 A1 | 3/2008 |
| WO | 2009021919 A2 | 2/2009 |
| WO | WO 2009/021919 * | 2/2009 |
| WO | 2009067682 A2 | 5/2009 |
| WO | WO 2011/110191 * | 9/2011 |
| WO | WO 2011144344 * | 12/2011 |
| WO | WO 2011/110343 * | 9/2017 |

OTHER PUBLICATIONS

Fridman et al., "Applied Plasma Medicine", Plasma Process. Polym., vol. 5, pp. 503-533 (2008).
International Search Report for PCT/EP2012/001923 dated Sep. 11, 2012.
Machine translation of DE 102 54 135 B3.
Machine translation of DE 202006009481 U1.

* cited by examiner

METHOD FOR DEACTIVATING PREFERABLY ODOR-RELEVANT MOLECULES AND DEVICE FOR CARRYING OUT SAID METHOD

BACKGROUND OF THE INVENTION

The invention concerns a method for deactivation of preferably odor-relevant molecules according to the invention, an apparatus for performance of a method for deactivation of preferably odor-relevant molecules according to the invention and an apparatus according to the invention.

It is known that a plasma can be used for disinfection, especially of surfaces contaminated with bacteria. Methods and apparatuses are known, by means of which surfaces are decontaminated or disinfected by plasma. Bacteria, germs, viruses, spores, fungi and other elements that make the surface nonsterile are then killed or deactivated by the plasma. The known methods and apparatuses, however, are not restricted to application to surfaces. Air volumes can also be disinfected in this way. Bacteria are often responsible for formation of unpleasant odors on surfaces or also in air volumes, metabolizing nutrients that are present and then producing substances with unpleasant odor. By killing or deactivating these bacteria it can at least be temporarily prevented that additional substances with unpleasant odors or other interfering molecules are formed. The already present substances, however, are not eliminated, so that their odor ordinarily must be masked or covered by additional substances. It is desirable to deactivate these substances. It is also desirable to deactivate other interfering, especially surface-associated molecules.

DESCRIPTION OF THE INVENTION

The underlying task of the invention is therefore to provide a method and apparatus with which especially odor-relevant molecules can be deactivated.

This task is solved by the method according to the invention. This is characterized by the following steps: plasma is generated and preferably odor-relevant molecules are deactivated by the action of hot electrons of the plasma on the molecules being deactivated. The term "deactivation" then means that the molecules, for example, are dissociated by the hot electrons or altered in their molecular structure or that reactions, for example, addition reactions, are made possible by the hot electrons, through which the molecules are altered so that they are no longer odor-relevant or otherwise interfering. The term "odor-relevant" means that the molecules themselves have an unpleasant odor, can react with additional molecules so that unpleasant odors are formed, so that they are also odor-forming and/or that they serve as a nutrient for bacteria, which synthesize odor-relevant molecules from it. The term "molecules" also includes odor-relevant or otherwise interfering substances that are not present in molecular form. The term "hot electrons" means electrons that are present in the immediate area of the plasma, i.e., the quasi-neutral, ionized gas or state of aggregation and which have a velocity distribution that is either nonthermal, in which case an average velocity of the electrons corresponds to a kinetic energy of at least one, preferably several electron volts, or their velocity distribution is thermal, in which case the temperature that can be assigned to the distribution lies well above 25° C. and preferably so high that the average kinetic energy of the electrons is an electron volt to several electron volts. In any case the average kinetic energy of the electrons is preferably sufficient to deactivate especially odor-relevant molecules. With particular preferably the average kinetic energy of the electrons is sufficient in order to dissociate especially unpleasantly smelling molecules. It was found that precisely large molecules had dissociation cross sections or dissociation energies that are suitable for the method. It is therefore especially possible to deactivate large molecules, like protein molecules.

Preferably odor-relevant molecules attached to a surface are deactivated, especially before they can be distributed in the surroundings. Surfaces, for example, skin surfaces, are frequently loaded with odor-relevant or otherwise interfering molecules that are almost surface-associated. These are deactivated with particular advantage by means of the method. The method is particularly effective in this case because a given surface density of molecules can be reduced by means of a given electron flux more simply and in a shorter time based on the relevant effect cross sections than is the case at a corresponding volume density of the molecules.

With particular preference the plasma is generated at a distance to the surface being treated, the distance being chosen so that an effect of the electrons on the surface-associated molecules is guaranteed. This means that the density for flow of hot electrons diminishes sharply with distance to a plasma source or location of formation of the actual plasma. The generation location of the plasma must therefore be positioned close enough to the surface being treated that sufficiently hot electrons are available for deactivation of the surface-associated molecules.

A method is particularly preferred in which, in addition to deactivation of preferably odor-relevant molecules, bacteria, preferably odor-forming bacteria or bacteria that form other interfering molecules are killed by the plasma. The term "plasma" here includes not only plasma in the narrower sense, i.e., a quasi-neutral at least partially ionized gas, which includes hot electrons, but also reactive species generated by the plasma, for example, excited and/or reactive molecules, radicals of other active species whose range is greater than that of hot electrons. Such reactive species, which are assigned to the plasma in the broader sense, can kill bacteria especially on a surface being treated. Because of this, in addition to deactivation of preferably odor-relevant molecules, it is avoided at the same time that new undesired molecules are formed by the metabolism of any bacteria present.

In this context a method is also preferred in which the distance of plasma generation to a surface being treated is chosen as a function of the desired effect mechanism. In particular, by choosing the distance a dominant effect mechanism can be set: if the distance is chosen small, the deactivation effect of especially odor-relevant molecules by hot electrons dominates. If the distance, on the other hand, is chosen larger, the bactericidal effect based on reactive species included by the plasma in the broader sense dominates. The distance is preferably chosen so that both effects are as effective as possible.

A method is also preferred in which the surface is chosen from skin, textile material, ceramic, plastic or leather. As an alternative or at the same time an additive to be applied to the surface being treated is chosen from at least one deodorant and/or an antiperspirant. The term "deodorant" then means substances that serve essentially to mask, cover or deactivate odor-relevant substances. The term "antiperspirant" means substances that essentially serve to prevent perspiration, for example, by having an astringent effect on skin areas containing sweat pores. If the method is used to treat skin, the armpits or pubic area are meant with particular preference.

A method is also preferred in which non-odor-relevant molecules are deactivated, especially those that cause discomfort, a sick feeling, disease, weakness or similar conditions. These include allergens, protein molecules or prions. Such molecules are also referred to here for short as "interfering molecules". The term "non-odor-relevant" means that the interfering effect of these molecules does not primarily consist of the fact that they have an unpleasant odor. However, it is not ruled out in any case that the molecules mentioned here also have an unpleasant odor in addition to their primary effect.

Finally, a method is preferred in which molecules are deactivated in a fluid stream of an apparatus that is provided to generate and/or convey a fluid stream. The apparatus is then preferably designed as a suction hood, especially a fume hood, gas scrubbing device, apparatus for conveyance of liquids, especially a tap system or faucet, vacuum cleaner, hair dryer, steam-jet ejector or hand dryer. It is therefore possible to deactivate interfering molecules, whether they are odor-relevant or otherwise unpleasant or even health-hazardous directly in the fluid stream of such an apparatus before they are supplied to their actual use or their destination.

The task is also solved by devising an apparatus with the features of the invention. This serves for performance of a method for deactivation of preferably odor-relevant molecules and includes a housing, a plasma source connected to the housing and at least one spacer. It is characterized by the fact that the at least one spacer is provided on the housing and/or the plasma source so that at least in areas a distance can be maintained between the plasma source and a surface being treated, in which molecules attached to the surface being treated are deactivated by hot electrons in the plasma. The comments concerning the method are referred to for definitions. It is essential that the spacer be provided so that at least in areas a distance already described in conjunction with the method can be maintained at which sufficient flow of hot electrons is available in order to deactivate surface-associated or preferably odor-relevant molecules.

The spacer is preferably designed adjustable. It is therefore possible to select an effect mechanism or at least a dominant effect mechanism. The emphasis for treatment by means of the apparatus can then either be deactivation or preferably odor-relevant molecules or the bactericidal effect described in conjunction with the method.

The plasma source preferably has a surface in whose area the plasma is generated.

This surface can preferably be curved, preferably designed convex or concave. In this case a distance is preferably produced at least in areas to the surface being treated by curvature of the surface, which corresponds to a desired distance with respect to the mentioned effect mechanisms when the surface of the plasma source lies on the surface being treated at least in areas.

The surface of the plasma source and the spacer are preferably arranged so that together they can enclose a closed volume with a surface being treated.

This produces particularly efficient and rapid treatment of the surface areas that delimit the closed volume.

The closed surface with particular preference is adjustable by making the elastic surface of the plasma source flexible and/or elastic and cooperating accordingly with the adjustable spacer. By adjusting the spacer the flexible or elastic surface of the plasma source is then bendable, expandable or reducible so that ultimately the volume to be enclosed with the surface being treated is adjusted.

With particular preference an application means is also provided, which is suitable or designed to apply a preferably liquid additive, for example, a deodorant and/or antiperspirant to a surface being treated.

Finally, it is also preferred that the application means includes a spray, a roller device or a stick or pencil device.

The task is finally also solved by devising an apparatus with the features of the invention. This includes a plasma source and is designed for passage and/or generation of a fluid stream. The plasma source is designed and/or arranged so that molecules can be deactivated in the fluid stream.

A device, which is designed as a suction hood, especially a fume hood, a gas scrubber device, vacuum cleaner, hair blower, steam-jet ejector, device for conveyance of liquids, especially a tap system or faucet, or hand dryer, is particularly preferred. By means of the apparatus it is possible to deactivate odor-relevant or otherwise unpleasant optionally even health-hazardous molecules in the fluid stream before they are fed to their actual purpose or destination.

BRIEF DESCRIPTION OF THE DRAWINGS

The invention is further explained below with reference to the drawing. In the drawing:

FIG. 1 shows a schematic view of a first practical example of an apparatus suitable for performance of the method for deactivation of preferably odor-relevant molecules. In this case a plasma is generated by the apparatus, in which preferably odor-relevant molecules are deactivated by the action of hot electrons in the plasma on the molecules being deactivated.

Figure 1:
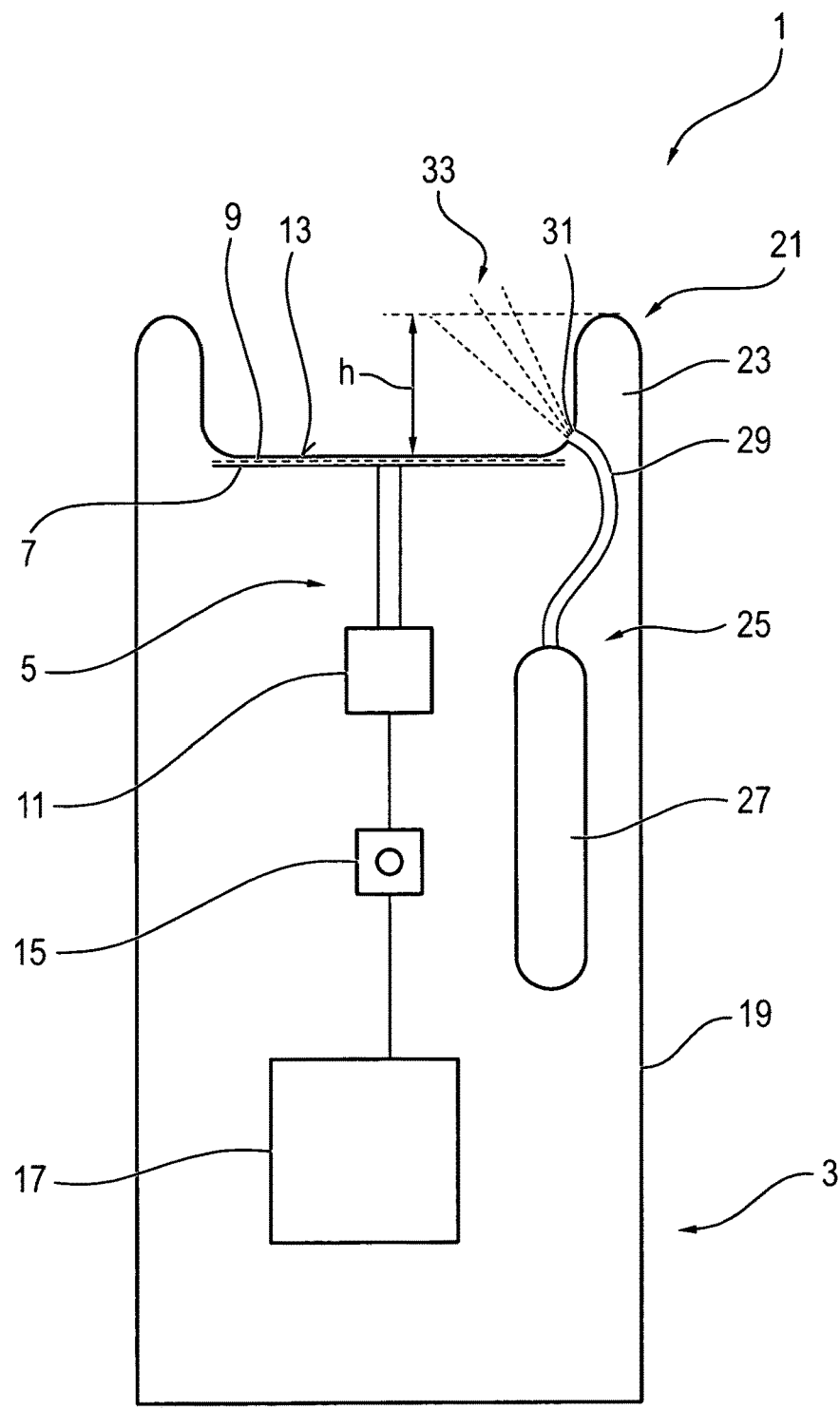
FIG. 1 shows a schematic view of a first practical example of an apparatus for performance of a method for deactivation of preferably odor-relevant molecules.

The apparatus 1 includes a housing 3 and a plasma source 5 connected to the housing. This is arranged in housing 3. It is preferably also possible to arrange the plasma source 5 on the housing 3 so that this serves as a support for plasma source 5.

Plasma sources are generally known. It is possible to use a plasma source 5 that includes only an electrode acted upon with alternating voltage, preferably a high frequency alternating voltage. In this case the surface being treated serves as counterelectrode, a plasma being ignited between the electrodes. This corresponds to the principle of a dielectric barrier discharge (DBD). It is also preferably possible to use a plasma source including two electrodes, one of which is acted upon with alternating voltage, the other preferably being grounded. To guarantee safety of the user the grounded electrode is then preferably provided on a surface facing the surface being treated. The two electrodes are spaced from each other by a dielectric. A discharge is ignited between the electrodes so that a plasma is formed on the side of the electrode facing the surface being treated, which acts on the surface being treated. This corresponds to the principle of surface micro discharge (SMD). Finally, it is preferably also possible to provide a plasma source in which both electrodes are embedded in at least one dielectric. The electrode facing the surface being treated is then so close to the surface of the dielectric that a plasma is formed on the surface when a discharge is ignited between the electrodes. The electrode is also preferably grounded in this case, which faces the surface being treated. Since both electrodes are embedded in at least one dielectric, no electrode is freely accessible. This corresponds to the principle of a self-sterilizing surface (SSS).

In the practical example shown in the figures a plasma source is schematically indicated that satisfies the principle of self-sterilizing surface. This corresponds to a preferred embodiment; it is likewise also possible to provide another plasma source.

The plasma source 5 includes a first electrode 7 and a second electrode 9. Both electrodes are connected to a voltage source 11 so that the first electrode 7 is acted upon with high voltage at appropriate frequency, the second electrode 9 preferably being grounded. Both electrodes 7, 9 are preferably embedded in a dielectric, the second electrode 9 being arranged somewhat below a surface 13 in whose area a plasma is generated when a discharge is ignited between electrodes 7, 9.

In particular, when the surface being treated is skin, a plasma source is preferred in which the skin does not serve as counterelectrode. Thus, a possibly unpleasant exposure of the skin to current is avoided.

Apparatus 1 preferably includes a switch 15, via which the plasma source 5 can be activated and/or deactivated. It also preferably includes a power supply 17, through which the voltage source 11 can be supplied with power. The power supply 17, as shown here as an example, can be designed as a battery, storage battery or other power supply connected to housing 3. However, it is preferably also possible to provide a connection for an external power supply, for example, a plug. It is also possible to supply the plasma source 5 via an energy-harvesting device. In this case piezocrystals, permanent magnets movable in coils, devices based on the principle of thermoelectricity, for example, Seebeck effect, Peltier effect and/or Thomson effect, solar panels and numerous other known apparatuses are considered. These are sometimes preferably integrated in the voltage source 11 or replace it. For example, a piezocrystal could be provided, which simultaneously serves as voltage source and power supply.

If the apparatus 1 is designed as a portable or handheld device, it preferably has a gripping area 19. A nonslip surface is provided in this area so that a user can securely grasp the apparatus 1.

The apparatus 1 also includes a spacer 21. In the depicted practical example this is provided on housing 3 so that a distance can be maintained between the plasma source 5 (here specifically surface 13) and a surface being treated (not shown). The apparatus 1 is preferably supported by means of the spacer 21 on the surface being treated (not shown) so that corresponding distance is maintained. This distance is defined here by the height h by which the highest point of the spacer 21 extends above surface 13. The distance or height h is chosen so that molecules attached to the surface being treated are deactivated by hot electrons of the plasma. For this purpose the distance is preferably between 0 and 4 mm, preferably between 1 and 3 mm and especially 2 mm. A distance that is less than 2 mm is also preferably. It is then ensured that the flux of hot electrons reaching the surface being treated is sufficiently large to deactivate associated, especially odor-relevant or other interfering molecules there.

The distance shown purely schematically in FIG. 1 or height h is shown somewhat exaggerated relative to the total size of apparatus 1.

The spacer 21 in the practical example depicted in FIG. 1 is designed as a collar 23. This is preferably designed in one piece with housing 3. However, it is preferably also possible to form the spacer 21 separately from the housing 3 and arrange it or fasten it appropriately to it.

The apparatus depicted in FIG. 1 is preferably designed with cylindrical symmetry. In this case the collar 23 also preferably extends fully in the peripheral direction of apparatus 1.

It is preferably also possible that individual spacers are arranged on housing 3 instead of the annular collar 23, which are distributed preferably symmetrically, that is with constant angular distance when viewed along the peripheral direction. For example, two opposite spacers can be provided. It is also possible to provide more than two spacer elements.

The collar 23 closed in a ring however, is advantageous as spacer 21 when in this case the surface 13 and the spacer 21 are arranged so that a closed volume can be enclosed by it and a surface being treated. This is especially the case when the surface being treated lies fully on the highest elevation of the spacer 21 (viewed in the peripheral direction). In this case particularly rapid and efficient treatment of the surface is possible because no interfering effects, like air currents acting from the outside, develop.

The apparatus 1 preferably also includes an application device 25 to apply a preferably liquid additive to the surface being treated. In the depicted practical example the application device 25 is designed as a spray, which includes a supply container 27, a feed line 29 and an outlet 31. A pump device is not shown, which the application device 25 preferably includes in order to drive out an additive from the supply vessel 27 via the feed line 29 through outlet 31. The supply vessel 27 is preferably refillable and/or replaceable and arranged in or on the container 3. By means of the application device 25 it is preferably possible to apply at least one additive to the surface before, after or also during treatment of the surface being treated with the plasma source 5. A spray mist 33 of the at least one additive discharged from outlet 31 is schematically shown here. It is possible to activate the application device 25 together with the plasma source 5 via switch 15. In another practical example it is proposed to activate the application device 25 separately via its own activation device. Continuous operation or pulse operation, for example, in the fashion of a pump spray, is then possible for the application device 25.

The application device 25 can also be designed as a roller device in the fashion of a deodorant roller, or also a stick device, for example, a pencil device in which a stick or pencil for application of at least one additive is provided, which is spread in known fashion over the surface being treated. A device is then preferably provided by means of which the stick or pencil can be moved in order to further feed it when it is consumed and therefore becomes smaller.

The at least one additive preferably includes a perfume. This is preferably applied after deactivation of especially odor-relevant molecules on the treated surface. It then imparts a pleasant odor to the surface and can cover or mask any residues of a foul odor still present. Any remaining "technical" odor produced by the plasma can also be covered or masked in this way.

Figure 2:
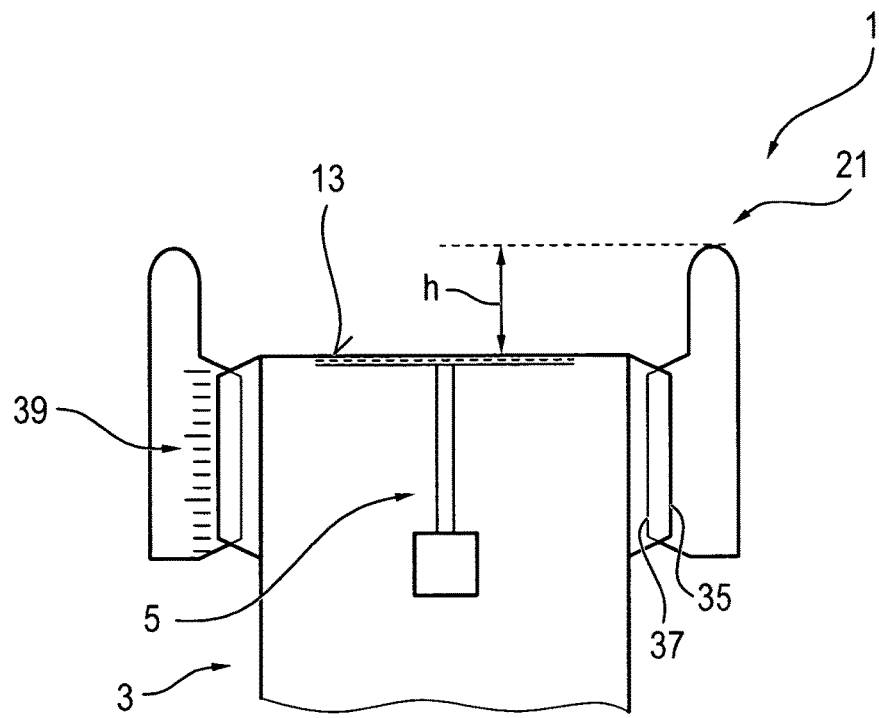
FIG. 2 shows a schematic view of a second practical example of the apparatus.

FIG. 2 shows a schematic view of a second practical example of the apparatus. Identical and functionally identical elements are provided with the same reference numbers so that in this respect the previous description is referred to. The spacer 21 is designed adjustable here. For this purpose an outside thread 35 is provided in the depicted practical example on housing 3, which meshes with inside thread 37 of the spacer 21. By rotating the spacer 21 relative to housing 3 the height h can be adjusted. The distance between surface 13 and the surface being treated (not shown) is therefore also varied.

During treatment of surfaces with respect to avoidance of foul odors or elimination of interfering molecules, as already stated, two mechanisms are relevant and particular: in the first place odor-relevant molecules can be deactivated by hot electrons in the plasma and in the second place it is possible to deactivate or kill bacteria present on the surface as source of interfering molecules by means of reactive species of the plasma in the broader sense on the surface. The first mechanism, which is based essentially on electron dissociation of molecules, is particular relevant at small distances. The second mechanism is relevant at somewhat larger distances in which the preferably excited, but reactive species are present. By means of adjustable spacer 21a choice can be made between effect mechanisms or a compromise is preferably made between the effectiveness of both mechanisms. In extreme cases the spacer 21 can be adjusted so that only the electron dissociation mechanism is active or a large enough height h can be set so that only the bactericidal effect is active. A middle adjustment is preferably chosen between these extremes.

In order to assist the user in adjusting the spacer 21a scale 39 is preferably provided on it. This can preferably include division lines, indicating height h. As an alternative, symbols can also be provided which code the set effect mechanism or mixed forms thereof.

Instead of thread 35, 37 it is proposed in another practical example to use means with which the spacer 21 can be pushed onto housing 3 and preferably locked in fixed positions. For example, a type of snap device can be provided. Such adjustment devices are known, for example, from hair clippers. Continuous adjustability of the spacer 21 can also be provided so that relatively high friction is present between housing 3 and spacer 21 so that the user can adjust a defined height h by relative displacement of the spacer 21 and housing 3.

Figure 3:
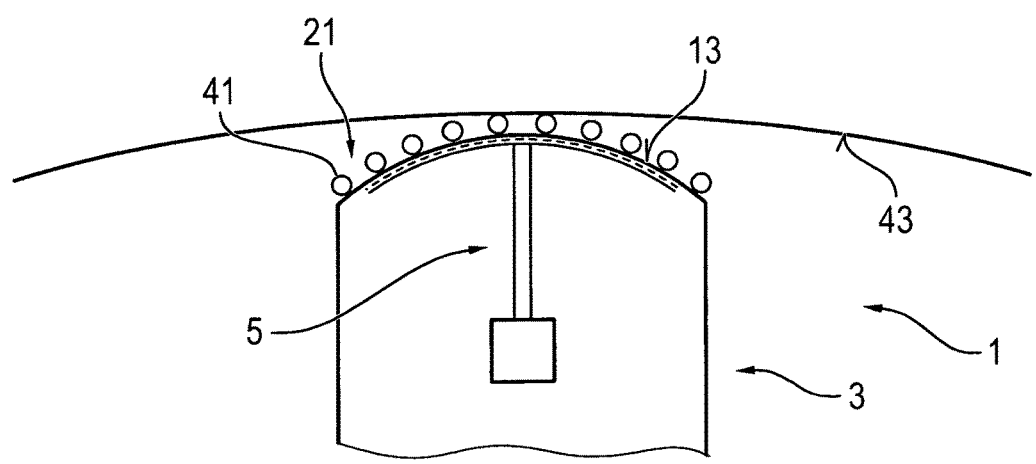
FIG. 3 shows a schematic view of a third practical example of the apparatus.

FIG. 3 shows a schematic depiction of a third practical example of the apparatus. Identical and functionally identical elements are provided with the same reference numbers so that to this extent the previous description is referred to. In the depicted practical example the surface 13 of the plasma source 5 is curved, namely designed convex. In other practical examples a different also irregular curvature is possible. Convex curvature of surface 13 has the advantage that there are always different distances from surface 13 to a surface 43 being treated if this has a radius of curvature different from surface 13. Different effect mechanisms can thus be active in different areas of surface 13 or the surface 43 being treated. If the apparatus 1 depicted in FIG. 3 is designed with cylindrical symmetry, the distance between surface 13 and surface 43 diminishes radially inward. In a radially inner lying area a distance is then preferably present at least in areas in which sufficient flux of hot electrons to the surface 43 is guaranteed in order to deactivate molecules there. Areas in which the bactericidal effect of reactive species dominates are preferable radially outward. If the entire surface 43 to be treated is covered by means of apparatus 1, both effect mechanisms are active at all sites of the surface 43 without requiring a change in apparatus 1, for example, adjustment of a spacer.

In order to guarantee minimum distance between surface 13 and the surface 43 being treated, however, it is preferred to also provide a spacer 21 in this practical example. In the depicted practical example this includes protrusions arranged on the surface 13 and one protrusion of which is designated with reference number 41 as an example. The height of protrusion 41 above the surface 13 is preferably chosen so that efficient treatment of the surface being treated in the context of electron dissociation especially of odor-relevant molecules is guaranteed when the surface 43 being treated lies at least in areas on the protrusions 41. In other practical examples other spacers 21 are provided: for example, ribs, grids, circular structures or similar spacers can be provided. It is also possible to design the surface 13 recessed in the areas in which plasma is formed so that areas of the surface 13 remaining between the recesses act as spacers 21.

Figure 4:
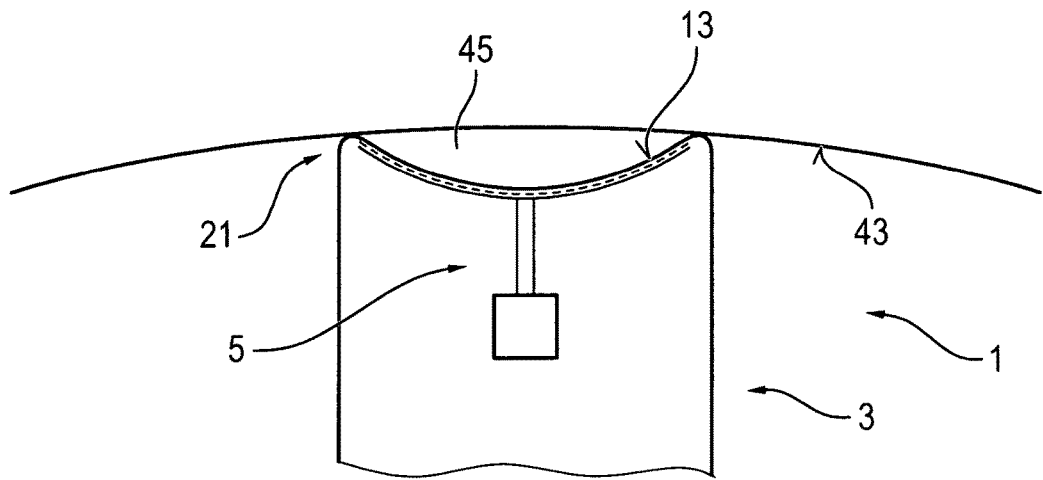
FIG. 4 shows a schematic view of a fourth practical example of the apparatus and FIG. 5 shows a schematic view of a fifth practical example of the apparatus.

FIG. 4 shows a schematic depiction of a fourth practical example of apparatus 1. Identical and functionally identical elements are provided with the same reference numbers so that to this extent the previous description is referred to. In the depicted practical example a surface 13 is designed concave. In the first place this has the advantage that corresponding concave surfaces can be treated simply by means of the apparatus 1. In the second place, however, in conjunction with a surface 43 being treated there is the advantage that the highest point of surface 13 itself becomes a spacer 21. The surface 43 being treated lies almost at the highest point of surface 13 so that the distance to the lowest point of surface 13 is stipulated. Its curvature can then be preferably chosen so that a specific effect mechanism or a specific distribution of effect mechanisms over surface 13 is achieved.

For example, it is possible to choose the lowest point of surface 13 so that exclusively deactivation of especially odor-relevant molecules occurs from hot electrons. However, it is also possible to choose the lowest points so that in this area a bactericidal effect is preferably or exclusively active due to reactive species on the surface 43 being treated, whereas (with assumed cylindrical symmetry of apparatus 1) in the areas located radially outside but in areas of surface 13 arranged closer to surface 43 an effect mechanism is established in which hot electrons contribute to deactivation of especially odor-relevant molecules. In this practical example by covering the entire surface 43 being treated with apparatus 1 it can therefore also be guaranteed that both effect mechanisms are active at each location of surface 43.

It is also found that in the practical example depicted in FIG. 4 the surface 13 and the spacer 21, namely their highest point and their highest peripheral line are arranged so that a closed volume 45 can be enclosed by them and by the surface 43 being treated. As already stated, this has the advantage that particularly rapid deactivation of especially odor-relevant molecules and also particularly rapid killing or deactivation of bacteria, which form foul odors and/or other interfering molecules, it is possible because no interfering effects from the outside can penetrate into closed volume 45.

Figure 5:
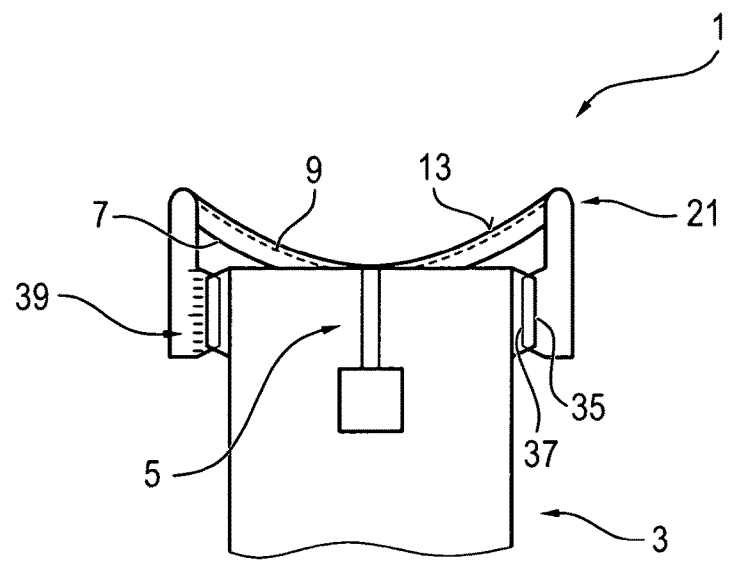

FIG. 5 shows a schematic view of a fifth practical example of apparatus 1. Identical and functionally identical elements are provided with the same reference numbers so that to this extent the previous description is referred to. In the depicted practical example the surface 13 is designed flexible and preferably also elastic. For example, a rubber or rubber-like elastic material can be chosen for this area of plasma source 5. Electrodes 7, 9 with particular preference are integrated in the flexible and/or elastic material and preferably are themselves made flexible and/or elastic.

In the depicted practical example the surface 13 cooperates with the adjustably designed spacer 21 here so that the volume that can be enclosed with a surface being treated (not shown) is adjustable. If the spacer 21 in FIG. 5 is moved upward, at least wall areas of surface 13 are moved upward together with it. For this purpose the surface 13 is connected to the spacer 21 at least on an outer annular area. A central area of surface 13 is preferably connected to housing 3 so that this area is always arranged in a constant position relative to housing 3 even when the spacer 21 is adjusted. Only wall areas of the surface 13 then are moved together with spacer 21. In particular, the wall areas during displacement of spacer 21 are expanded upward and pulled together again during its movement downward. Overall it is therefore found that not only the volume enclosed by surface 13 in the surface being treated is adjustable, but so is the relevant distance from the surface being treated to the lowest point of surface 13. It is therefore possible to select between different effect mechanisms or distributions of effect mechanisms over surface 13 in the manner already described.

For this purpose it is also possible in the practical example depicted here to provide scale 39 on the spacer 21.

The apparatus 1 and especially the method are not restricted to the practical examples depicted here. The method and apparatus can be used anywhere foul odor, the presence of interfering molecules or their formation is to be prevented. This can be the case, for example, on the human body. In this case the armpits, the pubic area and/or the feet are considered in particular, the application not being restricted to these body areas. The surface being treated then preferably includes skin.

With quite particular preference the apparatus 1 is designed as a deodorant device. An application device 25 is then also preferably provided through which additives can be applied to the skin. These preferably include at least one deodorant and/or at least antiperspirant.

The method and apparatus 1 can be used in general in order to mask, modify, reduce or prevent body odors or foul odors from persons. This can also be foul odors that are caused by incontinence and/or escape from the interior of the body.

However, the method is not restricted in particular to treatment of surfaces. It can also find application in suction hoods, especially fume hoods, gas scrubber devices, vacuum cleaners, hair dryers, steam-jet ejectors, devices for conducting gases, vapors, dusts, liquids or other fluids, especially tap systems or faucets, hand dryers or similar devices. It need only be ensured that sufficient density of molecules to be deactivated is acted upon with a sufficient flux of hot electrons so that noticeable deactivation of the molecules occurs. For example, narrow channels within a line for gases, vapors, dust, liquids or other fluids can be provided, within which corresponding deactivation of especially odor-relevant molecules occurs.

In this context an apparatus is preferred with which the method can be conducted and which conveys and/or generates a fluid stream. It includes a plasma source, which is designed and/or arranged so that it can deactivate molecules, especially odor-relevant or otherwise interfering molecules in the fluid stream. The fluid stream preferably involves gases, vapors, dust, liquid or other fluids. The apparatus is preferably designed as a suction hood, especially an fume hood, a gas scrubber device, vacuum cleaner, hair dryer, steam-jet ejector, device for conveying liquids, especially a tap system or hand dryer. It is also possible for the apparatus to be designed as a faucet.

In another case it is possible with the apparatus to deactivate odor-relevant or otherwise interfering optionally health-hazardous molecules in the fluid stream before it is fed to its actual purpose or reaches its destination. With particular preference the electrode of the plasma source in whose area the plasma is generated, is arranged on a surface or embedded in it, which has direct contact with the fluid stream. In order to ensure that sufficient density of molecules to be inactivated is acted upon with a sufficient flux of hot electrons, narrow channels are preferably provided for conveying the fluid stream. In this case the corresponding electrode is preferably arranged on a surface of these channels or embedded in them. The plasma is formed directly on a channel surface so that interfering molecules can be efficiently deactivated. The plasma generated by the plasma source naturally also has a bactericidal or disinfecting and/or sterilizing effect within the apparatus. Germs, fungi, spores, bacteria and viruses are therefore efficiently deactivated in the fluid stream.

It is possible in all variants and practical examples to add additive to the plasma itself, which have a special effect in conjunction with the plasma. These can be gases, catalysts and/or medicinally active ingredients, which either contribute to activation of components of the plasma, through which the plasma itself is activated or catalyze certain reactions or contribute to certain effects on the surface being treated. These additives can be introduced in front of, behind and between the electrodes into a diffusion or flow path of the plasma. It is also possible to apply these additives by means of the application device 25 on the surface being treated.

It is possible that a surface being treated includes textile material, ceramics, plastic and/or leather. For example, clothing can be free of foul odors and/or interfering molecules by means of the method and/or apparatus 1. In particular, in conjunction with textile material, for example, clothing and generally in conjunction with materials including fibers, the term "surface" here is to be understood in a broader sense. The plasma and the hot electrons have a certain penetration depth in such materials so that the immediate surface is not exclusively treated but there is a depth effect that can include the entire treated layer of material. Such materials can be effectively freed of foul odors and/or interfering molecules by means of apparatus 1 and the method.

Apparatus 1 and the method are also usable in conjunction with toilets, sinks or other ceramic apparatus on whose surfaces foul odors or interfering molecules can form. This applied in particular to plastic, for example, in the kitchen or also leather, for example in the living area. Carpets and rugs, stairways, walls, generally all household surfaces, but also commercial surfaces are also treatable with the method and apparatus 1. An additive that can preferably be applied by means of application device 25 can then preferably be a cleaning agent or care agent.

Finally, the apparatus 1 and the method are usable in particular in conjunction with shoes. The apparatus 1 and the method are preferably used in the interior of shoes. For this purpose the apparatus 1 can preferably have the form of a shoe tree or an insole, be designed as a shoe tree or insole or also be integrated in a shoe tree or insole. For example, it is possible to provide recesses in the surface of a shoe tree in which the plasma is generated. The unrecessed surface area then functions as spacer 21. It is also possible to provide protrusions as spacers 21 on the surface. The surface of apparatus 1 on which the plasma is generated preferably follows the contour of the shoe so that large-area treatment is present. However, a side of the shoe sole facing the foot is treated with particular preference so that it can be sufficient in one practical example to provide a plasma source only in this area. In particular, plasma to degenerate foul odors or other interfering molecules can be generated in the lower area of the shoe tree in the intermediate space between a surface of the shoe tree facing a sole and the sole.

The bactericidal effect of apparatuses and the method were tested and demonstrated for in particular in conjunction with the bacterium *Corynebacterium jeikeium* responsible for foul body odor. With reference to controlling foul odors a so-called sniff test was conducted in which test subjects were given skin areas and textiles treated with a foul smelling solution in the context of a blind experiment as smelling test in which the samples were sometimes treated with the apparatus and with the method and sometimes untreated. It clearly turned out that the treated skin areas or textiles smelled better than the untreated one. Any detectable "technical" odor, produced by the plasma, can be masked by at least one appropriate additive.

It is therefore found overall that the method and apparatuses are especially suitable for reducing foul odors, preventing their formation or slowing it and ultimately for also reducing growth conditions for odor-forming bacteria and deactivation of their nutrient source. In combination with additives an additional masking effect of foul odors is possible. The method and apparatuses therefore close a gap, because thus far it has only been possible to treat the causes of formation of foul odors but not to eliminate the foul odors themselves. Deactivation of other interfering molecules is also possible.

In particular, everything stated with reference to the method and apparatuses in conjunction with odor-relevant molecules is also relevant accordingly in conjunction with the activation of other interfering molecules.

The invention claimed is:

1. A method for deactivation of odor-relevant molecules associated with a material to be treated, said method comprising the following steps:
   providing a plasma source comprising an electrode and a counter-electrode, wherein the electrode and the counter-electrode are spaced apart from each other by a dielectric and face a same side of the material to be treated at a distance of 0 to 4 mm;
   igniting a discharge so as to generate a plasma at the distance of 0 to 4 mm from the side of the material toward which both the electrode and the counter-electrode face; and
   applying to the odor-relevant molecules hot electrons of the plasma so as to deactivate the odor-relevant molecules by an electron dissociation mechanism which alters molecular structures of the odor-relevant molecules, wherein: (a) the hot electrons are electrons that have an average kinetic energy of at least one electron volt, and (b) the material to be treated is a textile material.

2. The method according to claim 1, wherein the odor-relevant molecules are attached to a surface.

3. The method according to claim 1, wherein bacteria are killed by the plasma.

4. The method according to claim 1, wherein the distance is chosen to balance a bactericidal effect based on reactive species of the plasma against an odor-relevant molecule deactivation effect based on the hot electrons of the plasma.

5. The method according to claim 2, wherein an additive is applied to the surface.

6. The method according to claim 5, wherein the additive is a deodorant and/or antiperspirant.

7. The method according to claim 1, further comprising a deactivation of non-odor-relevant molecules which are allergens.

8. A method for deactivation of odor-relevant molecules associated with a material to be treated, said method comprising the following steps:
   providing a plasma source comprising an electrode, a counter-electrode and a dielectric, wherein the electrode and the counter-electrode are spaced apart from each other by the dielectric and face a same side of the material to be treated;
   igniting a discharge so as to generate a plasma on the side of the material towards which both the electrode and the counter-electrode face, wherein the plasma is in contact with the material; and
   applying to the odor-relevant molecules hot electrons of the plasma so as to deactivate the odor-relevant molecules by an electron dissociation mechanism which alters molecular structures of the odor-relevant molecules, wherein the hot electrons are electrons that have an average kinetic energy of at least one electron volt, wherein: (a) the odor-relevant molecules are in a fluid stream in a device that generates or conveys a fluid stream, and (b) the material to be treated is a textile material.

9. The method according to claim 1, wherein the odor-relevant molecules are predominantly deactivated by hot electrons of the plasma.

* * * * *